United States Patent
Honjo et al.

(10) Patent No.: US 7,273,725 B2
(45) Date of Patent: *Sep. 25, 2007

(54) HUMAN AND MAMMALIAN STEM CELL-DERIVED NEURON SURVIVAL FACTORS

(75) Inventors: Tasuku Honjo, 19-4, Ohsagi-cho, Iwakura, Sakyo-ku, Kyoto-shi, Kyoto (JP) 606-0001; Kei Tashiro, Kyoto (JP); Jun Takahashi, Kyoto (JP); Hiroki Toda, Palo Alto, CA (US)

(73) Assignees: Ono Pharmaceuticals Co., Ltd., Osaka (JP); Tasuku Honjo, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/493,393

(22) PCT Filed: Oct. 22, 2002

(86) PCT No.: PCT/JP02/10936

§ 371 (c)(1),
(2), (4) Date: Apr. 22, 2004

(87) PCT Pub. No.: WO03/035872

PCT Pub. Date: May 1, 2003

(65) Prior Publication Data

US 2004/0248137 A1    Dec. 9, 2004

(30) Foreign Application Priority Data

Oct. 23, 2001   (JP)   ............................. 2001-325189

(51) Int. Cl.
  *C12P 21/06*   (2006.01)
  *C07K 14/00*   (2006.01)
(52) U.S. Cl. ................ 435/69.1; 435/70.1; 530/350
(58) Field of Classification Search ............ None
  See application file for complete search history.

(56) References Cited

U.S. PATENT DOCUMENTS

| 4,677,099 | A  | * | 6/1987 | Shinitzky et al. | .............. 514/78 |
| 6,605,592 | B2 | * | 8/2003 | Ni et al. | ........................ 514/2 |
| 2005/0064543 | A1 | * | 3/2005 | Tang et al. | ................ 435/69.1 |

FOREIGN PATENT DOCUMENTS

| WO | 99/18204 A2 | 4/1999 |
| WO | 01/21658 A1 | 3/2001 |

OTHER PUBLICATIONS

Deka et al. Repetitive nucleotide sequence insertions into a novel calmodulin-related gene and its processed pseudogene Gene, vol. 71, No. 1, pp. 123-134, Nov. 1988.*

Zhang et al. Bleeding due to disruption of a cargo-specific ER-to-Golgi transplant complex. Nature Genetics, vol. 34, No. 2, pp. 220-225, Jun. 2003.*

Uniprot entry Q8NI22, printed on Jun. 27, 2005.*

Dirnagle et al. Pathobiology of ischaemic stroke: an integrated view. Trends Neurosci. vol. 22, No. 9, pp. 391-397, Sep. 1999.*

Agrawal et al. In situ stem cell therapy: novel targets, familiar challenges. Trends Biotechnol. vol. 23, No. 2, pp. 78-83, Feb. 2005.*

Recommendations for standards regarding preclinical neuroprotective and restorative drug development. Stroke. vol. 30, No. 12, pp. 2752-2758, Dec. 1999.*

Lees. Neuroprotection is unlikely to be effective in humans using current trial designs: an opposing view. Stroke. vol. 33, No. 1, pp. 308-309, Jan. 2002.*

Maurelli et al. Two novel classes of neuroactive fatty acid amides are substrates for mouse neuroblastoma 'anandamide amidohydrolase'. FEBS Letters, vol. 377, pp. 82-86, 1995.*

UniprotKB Entry: Q8K5B2 for Accession No. Q8K5B2, Sep. 5, 2006.*

Tiger et al. Pharmacological properties of rat brain fatty acid amidohydrolase in different subceullular fractions using palmitoylethanolamide as substrate. Biochemical Pharmacology, vol. 59, pp. 647-653, 2000.*

UniprotKB Entry: Q8K5B3 for Accession No. Q8K5B3, Sep. 5, 2006.*

Philippe Taupin et al., "FGF-2-Responsive Neural Stem Cell Proliferation Requires CCg, A Novel Autocrine/Paracrine Cofactor", Neuron (2000) vol. 28, pp. 385-397.

D. D. Sabatini et al., "The Signal Sequence Trap Method", Methods in Enzymology (1999) vol. 303, pp. 479-495.

Hiroki Toda et al., "Stem Cell-derived Neural Stem/Progenitor Cell Supporting Factor Is an Autocrine/Paracrine Survival Factor for Adult Neural Stem/Progenitor Cells", The Journal of Biological Chemistry (2003), vol. 278, No. 37, pp. 35491-35499.

Supplementary European Search Report dated Dec. 9, 2004.

* cited by examiner

Primary Examiner—Celine Qian
Assistant Examiner—Jennifer Dunston
(74) Attorney, Agent, or Firm—Sughrue Mion Pllc.

(57) ABSTRACT

The present invention relates to human, rat and mouse stem cell-derived neuron survival factor polypeptides (SDNSF), a process for producing them, cDNA encoding SDNSF, a vector comprising the cDNA, host cells transformed by the vector, an antibody against SDNSF, pharmaceutical compositions containing SDNSF or the antibody, a method of assaying SDNSF, a reagent for assaying SDNSF, and a screening method using SDNSF. The polypeptides are effective in the survival of nerve cells and, therefore, efficacious in treating injury to the central nerve system caused by brain infarction, brain hemorrhage, spinal cord injury, etc.

3 Claims, 6 Drawing Sheets

FIG. 1(A)

```
rSDNSF      1  MASLQLLRGPFLCVLLWAFCV-----PGARAQE-------HGA   31
mSDNSF      1  MATLQLLRAPLLCVLLWVFCA=====PGARAHD========HGA   31
hSDNSF      1  MTMRSLLRTPFLCGLLWAFCA-----PGARAEE--------PAA   31
NP_505967   1  MAANILVVS---CLILGSFAHQPQQFPGSNQQQPQQGGQAEQA   40
CG12817     1  MCNLSNLLNFICIASFSQNF-----DATLAVK-------RGP   31 rSDNSF     32  GVHH-GSVGLDKSTVHDQEHIMEHLEGVINQ-PEAEMSPQELQ   72
mSDNSF     32  DVHH-GSVGLDKSTVHDQEHIMEHLEGVIDQ-PEAEMSPQELQ   72
hSDNSF     32  SFSQPGSMGLDKNTVHDQEHIMEHLEGVINK-PEAEMSPQELQ   73
NP_505967  41  QHAQPGQQQFGGEQARDEHHIKEHLDGKVD==PTANMTPEQLQ   81
CG12817    32  HHPRGETRRVDQHLTHEEHRIDDDLKDMGVQANLDDLSEEEKI   74
                                EF hand 1
rSDNSF     73  LHYFKMHDYDGNSLLDGLELSTAITHVHKEE-G---------  104
mSDNSF     73  LHYFKMHDYDGNSLLDGLELSIAITHVHKEE-G---------  104
hSDNSF     74  LHYFKMHDYDGNNLLDGLELSTAITHVHKEE-G---------  105
NP_505967  83  FLHYFNMHDLDKNGKLDGVELIKATHFHAENPGPQHTQNNANA  134
CG12817    75  FYMFKAHDNDNNALDGLEMIQSAMHNYDYFK---------N  108
                                              EF hand 2
rSDNSF    105  SEQ-----VPPMSEDE-LISIIDGVLRDDDKMNDGYIDYAEFA  141
mSDNSF    105  SKQ-----APVMSEDE-LVSIIDGVLRDDDKMNDGYIDYAEFA  141
hSDNSF    106  SEQ-----APLMSEDE-LINIIDGVLRDDDKMNDGYIDYAEFA  142
NP_505967 125  NHQ-----PPPLPSEVE-LETMIDSILKDDDFMADGFIDYGEFL  162
CG12817   109  NERDAYL-QNATDELEHFIEALDKFLLIADDMNDGLLHYPEFV  150 rSDNSF    142  KSLQ                                         145
mSDNSF    142  KSLQ                                         145
hSDNSF    143  KSLQ                                         146
NP_505967 160  KAQKLREDQARSHQEQMQKAGGTQ                     106
CG12817   151  KAITGGKEQPNVDRNILR                           168
```

FIG. 1(B)

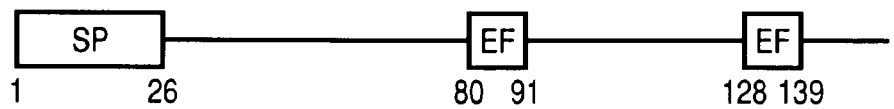

FIG. 2

```
                    HELIX          LOOP          HELIX
rSDNSF 1       LQLHYFKMHDYDGNSLLDGLELSTAITHV
rSDNSF 2       IIDGVLRDDDKNNDGYIDYAEFAKSLQ*
calmodulin 1   EFKEAFALFDKDGDGTITTKELGTVMRSL
calmodulin 2   ELQDMINEVDADGNGTIDFPEFLSLMARK
calmodulin 3   ELIEAFKVFDRDGNGLISAAELRHVMTNL
calmodulin 4   EVDEMIREADIDGDGHINYEEFVRMMVAK
consensus EF               DXDGDGXIIDXXE
```

*: P<0.01

*: P<0.01

SEQUENCE LISTING

<160> NUMBER OF SEQ ID NOS: 20

<210> SEQ ID NO 1
<211> LENGTH: 1771
<212> TYPE: DNA
<213> ORGANISM: Rattus rattus

<400> SEQUENCE: 1

```
gcgtcagggg gacgcagctg gcaaggttca tccacaagtg cttcgcgact gcgtcaggga      60
ttatcagggt actggaagca tggcatccct gcagctgctc agaggtccct tcctgtgtgt     120
tctgctctgg gccttttgtg ttcctggtgc cagggcccag gagcatgggg ctggtgtcca     180
ccatggcagc gtgggcctgg acaagagcac agtgcacgac aagagcacca ttatggaaca     240
tctggaaggt gtcatcaacc agccagaggc ggagatgtcc ccacaggaac tacagctcca     300
ttatttcaaa atgcatgatt acgatggcaa cagtttgctt gatggcttag agctctcgac     360
ggccatcact cacgtgcaca aggaggaggg gagtgagcag gtcccaccca tgagcgagga     420
cgagctcatc agcatcatag acggtgtcct gagagacgac gacaagaaca atgacggcta     480
catcgactat gcagagtttg ccaagtcgct gcagtaggcg gcaggccctt tcctgtatgc     540
acacgtgacc cttgctaatg tgatggacat tctggtaatg agaagcagct tatttctgtc     600
tactgctgca gcgctggtaa agcctgtggc agtctgttag actggggtag gaggaagcca     660
caaggaatac ggagagaagt ggggcagtgt caatgtgtgt ttaaacctgt tggacaagag     720
ctcgaacctt ccgaagggtg gtggggtatc tcaagctccc gggaacctga ctctagatgc     780
cactctaact tcttgatgtt atttcatgct acctgaaaag taaagacagt ctgctttgcc     840
aagtggagac ttcagtgacg gtggagggag agccaaaagc cgcgtatctt cccagttggg     900
tcctgctctg ggcagatgtg gtcagtatgc tgttccccag gcatacagca tcacgtccta     960
```

```
aagccacagc aggagaagaa tgtcacccac ggagtccacc agacacagag tgaagactcc    1020
ttacccactg gcattttgga agcgaagcac cactggcctg aatacttagc cttttcagat    1080
cttcagtttc cttcacaact actgccacac cctgtgctct gtcatttcag cccgagagaa    1140
accttgaatt gggtgtgctc tccgctcacc acccaccgtt tgagctccct gaccttgtgt    1200
tttatccttg ctcccagggc tcccttcttg gcttatgaac tattaacttg gtatcgcagg    1260
tttaaactgt cagctgctct agcctaagtc agaccagaaa agatcagtca ttaagggtgg    1320 tggctaaccct tatccaagtt ttgaaggaat gttttttaaaa ttacctcttt gagcctgaat    1380
atgataattc ttttaatttc agggaagaac agaaaaggaa gagcagtagt agctgaaaga    1440
gaaacagcca taggtcgtac tttgcgttgt gaaacgtcat agacttactg taaacgaatc    1500
cagaatgatg gtgggatcag aaaaagaaac tgaatcaaat ttgctttacg atgtatagag    1560
acttattttc tttattaaag tattcttgta agaaaactta cgtatttgta aaacagtttt    1620
ctgtgtcaag tatttgtgca atcggagctg acttgtaaac tattcttgta agatctcatt    1680
attttgaaag atttatataa tgaactctga ctatctgaca ataaaatgga tgaaaaagta    1740
aaaaaaaaaa aaaaaaaaaa aaaaaaaaaa a                                    1771

<210> SEQ ID NO 2
<211> LENGTH: 435
<212> TYPE: DNA
<213> ORGANISM: Rattus rattus

<400> SEQUENCE: 2
atggcatccc tgcagctgct cagaggtccc ttcctgtgtg ttctgctctg ggccttttgt      60
gttcctggtg ccagggccca ggagcatggg gctggtgtcc accatggcag cgtgggcctg     120
gacaagagca cagtgcacga ccaagagcac attatggaac atctggaagg tgtcatcaac     180
cagccagagg cggagatgtc cccacaggaa ctacagctcc attatttcaa aatgcatgat     240
tacgatggca acagtttgct tgatggctta gagctctcga cggccatcac tcacgtgcac     300
aaggaggagg ggagtgagca ggtcccaccc atgagcgagg acgagctcat cagcatcata     360
gacggtgtcc tgagagacga cgacaagaac aatgacggct acatcgacta tgcagagttt     420
gccaagtcgc tgcag                                                      435

<210> SEQ ID NO 3
<211> LENGTH: 1771
<212> TYPE: DNA
<213> ORGANISM: Rattus rattus
<220> FEATURE:
<221> NAME/KEY: CDS
<222> LOCATION: (80)..(514)
<220> FEATURE:
<221> NAME/KEY: sig_peptide
<222> LOCATION: (80)..(157)
<220> FEATURE:
<221> NAME/KEY: mat_peptide
<222> LOCATION: (158)..(514)

<400> SEQUENCE: 3
gcgtcagggg gacgcagctg gcaaggttca tccacaagtg cttcgcgact gcgtcaggga      60
ttatcagggt actggaagc atg gca tcc ctg cag ctg ctc aga ggt ccc ttc     112
                        Met Ala Ser Leu Gln Leu Leu Arg Gly Pro Phe
                        -25                 -20 ctg tgt gtt ctg ctc tgg gcc ttt tgt gtt cct ggt gcc agg gcc cag      160
Leu Cys Val Leu Leu Trp Ala Phe Cys Val Pro Gly Ala Arg Ala Gln
-15                 -10                  -5                  -1  1
```

| | | |
|---|---|---|
| gag cat ggg gct ggt gtc cac cat ggc agc gtg ggc ctg gac aag agc<br>Glu His Gly Ala Gly Val His His Gly Ser Val Gly Leu Asp Lys Ser<br>5 10 15 | | 208 |
| aca gtg cac gac caa gag cac att atg gaa cat ctg gaa ggt gtc atc<br>Thr Val His Asp Gln Glu His Ile Met Glu His Leu Glu Gly Val Ile<br>20 25 30 | | 256 |
| aac cag cca gag gcg gag atg tcc cca cag gaa cta cag ctc cat tat<br>Asn Gln Pro Glu Ala Glu Met Ser Pro Gln Glu Leu Gln Leu His Tyr<br>35 40 45 | | 304 |
| ttc aaa atg cat gat tac gat ggc aac agt ttg ctt gat ggc tta gag<br>Phe Lys Met His Asp Tyr Asp Gly Asn Ser Leu Leu Asp Gly Leu Glu<br>50 55 60 65 | | 352 |
| ctc tcg acg gcc atc act cac gtg cac aag gag gag ggg agt gag cag<br>Leu Ser Thr Ala Ile Thr His Val His Lys Glu Glu Gly Ser Glu Gln<br>70 75 80 | | 400 |
| gtc cca ccc atg agc gag gac gag ctc atc agc atc ata gac ggt gtc<br>Val Pro Pro Met Ser Glu Asp Glu Leu Ile Ser Ile Ile Asp Gly Val<br>85 90 95 | | 448 |
| ctg aga gac gac gac aag aac aat gac ggc tac atc gac tat gca gag<br>Leu Arg Asp Asp Asp Lys Asn Asn Asp Gly Tyr Ile Asp Tyr Ala Glu<br>100 105 110 | | 496 |
| ttt gcc aag tcg ctg cag taggcggcag gccctttcct gtatgcacac<br>Phe Ala Lys Ser Leu Gln<br>115 | | 544 |
| gtgacccttg ctaatgtgat ggacattctg gtaatgagaa gcagcttatt tctgtctact | | 604 |
| gctgcagcgc tggtaaagcc tgtggcagtc tgttagactg gggtaggagg aagccacaag | | 664 |
| gaatacggag agaagtgggg cagtgtcaat gtgtgtttaa acctgttgga caagagctcg | | 724 |
| aaccttccga agggtggtgg ggtatctcaa gctcccggga acctgactct agatgccact | | 784 |
| ctaacttctt gatgttattt catgctacct gaaaagtaaa gacagtctgc tttgccaagt | | 844 |
| ggagacttca gtgacggtgg agggagagcc aaaagccgcg tatcttccca gttgggtcct | | 904 |
| gctctgggca gatgtggtca gtatgctgtt ccccaggcat acagcatcac gtcctaaagc | | 964 |
| cacagcagga gaagaatgtc acccacggag tccaccagac acagagtgaa gactccttac | | 1024 |
| ccactggcat tttggaagcg aagcaccact ggcctgaata cttagccttt tcagatcttc | | 1084 |
| agtttccttc acaactactg ccacaccctg tgctctgtca tttcagcccg agagaaacct | | 1144 |
| tgaattgggt gtgctctccg ctcaccaccc accgtttgag ctccctgacc ttgtgtttta | | 1204 |
| tccttgctcc cagggctccc ttcttggctt atgaactatt aacttggtat cgcaggttta | | 1264 |
| aactgtcagc tgctctagcc taagtcagac cagaaaagat cagtcattaa gggtggtggc | | 1324 |
| taaccttatc caagttttga aggaatgttt ttaaaattac ctctttgagc ctgaatatga | | 1384 |
| taattctttt aatttcaggg aagaacagaa aaggaagagc agtagtagct gaaagagaaa | | 1444 |
| cagccatagg tcgtactttg cgttgtgaaa cgtcatagac ttactgtaaa cgaatccaga | | 1504 |
| atgatggtgg gatcagaaaa agaaactgaa tcaaatttgc tttacgatgt atagagactt | | 1564 |
| attttcttta ttaaagtatt cttgtaagaa aacttacgta tttgtaaaac agtttttctgt | | 1624 |
| gtcaagtatt tgtgcaatcg gagctgactt gtaaactatt cttgtaagat ctcattattt | | 1684 |
| tgaaagattt atataatgaa ctctgactat ctgacaataa aatggatgaa aaagtaaaaa | | 1744 |
| aaaaaaaaaa aaaaaaaaaa aaaaaaa | | 1771 |

<210> SEQ ID NO 4
<211> LENGTH: 145
<212> TYPE: PRT
<213> ORGANISM: Rattus rattus

<400> SEQUENCE: 4

```
Met Ala Ser Leu Gln Leu Leu Arg Gly Pro Phe Leu Cys Val Leu Leu
    -25             -20                 -15
Trp Ala Phe Cys Val Pro Gly Ala Arg Ala Gln Glu His Gly Ala Gly
-10              -5                -1  1                  5
Val His His Gly Ser Val Gly Leu Asp Lys Ser Thr Val His Asp Gln
             10                  15                  20
Glu His Ile Met Glu His Leu Glu Gly Val Ile Asn Gln Pro Glu Ala
                 25                  30              35
Glu Met Ser Pro Gln Glu Leu Gln Leu His Tyr Phe Lys Met His Asp
     40                  45                  50
Tyr Asp Gly Asn Ser Leu Leu Asp Gly Leu Glu Leu Ser Thr Ala Ile
 55                  60                  65                  70
Thr His Val His Lys Glu Glu Gly Ser Glu Gln Val Pro Pro Met Ser
                 75                  80                  85
Glu Asp Glu Leu Ile Ser Ile Ile Asp Gly Val Leu Arg Asp Asp
             90                  95                  100
Lys Asn Asn Asp Gly Tyr Ile Asp Tyr Ala Glu Phe Ala Lys Ser Leu
             105                 110                 115
Gln
```

```
<210> SEQ ID NO 5
<211> LENGTH: 823
<212> TYPE: DNA
<213> ORGANISM: Homo sapiens

<400> SEQUENCE: 5
tggtgaggcc cgaggcgttg gagggcttcg cgtctgcttc ggagaccgta aggatattga    60
tgaccatgag atccctgctc agaacccct tcctgtgtgg cctgctctgg ccttttgtg    120
ccccaggcgc cagggctgag gagcctgcag ccagcttctc ccaacccggc agcatgggcc    180
tggataagaa cacagtgcac gaccaagagc atatcatgga gcatctagaa ggtgtcatca    240
acaaaccaga ggcggagatg tcgccacaag aattgcagct ccattacttc aaaatgcatg    300
attatgatgg caataatttg cttgatggct agaactctc acagccatc actcatgtcc    360
ataaggagga agggagtgaa caggcaccac taatgagtga agatgaactg attaacataa    420
tagatggtgt tttgagagat gatgacaaga acaatgatgg atacattgac tatgctgaat    480
ttgcaaaatc actgcagtag atgttatttg gccatctcct ggttatatac aaatgtgacc    540
cgtgataatg tgattgaaca ctttagtaat gcaaaataac tcatttccaa ctactgctgc    600
agcattttgg taaaaacctg tagcgattcg ttacactggg gtgagaagag ataagagaaa    660
tgaaagagaa gagaaatggg acatctaata gtccctaagt gctattaaat accttattgg    720
acaaggaaaa acaacaaaaa aaatattag tctgtattaa tgctgctgat aaagacgtac    780
ccaagactgg gaagaaaaaa aaaaaaaaa aaaaaaaaa aaa    823
```

```
<210> SEQ ID NO 6
<211> LENGTH: 438
<212> TYPE: DNA
<213> ORGANISM: Homo sapiens

<400> SEQUENCE: 6
atgaccatga gatccctgct cagaaccccc ttcctgtgtg gcctgctctg gccttttgt     60
gccccaggcg ccagggctga ggagcctgca gccagcttct cccaacccgg cagcatgggc    120
```

```
ctggataaga acacagtgca cgaccaagag catatcatgg agcatctaga aggtgtcatc      180
aacaaaccag aggcggagat gtcgccacaa gaattgcagc tccattactt caaaatgcat      240
gattatgatg gcaataattt gcttgatggc ttagaactct ccacagccat cactcatgtc      300
cataaggagg aagggagtga acaggcacca ctaatgagtg aagatgaact gattaacata      360
atagatggtg ttttgagaga tgatgacaag aacaatgatg gatacattga ctatgctgaa      420
tttgcaaaat cactgcag                                                    438
```

```
<210> SEQ ID NO 7
<211> LENGTH: 823
<212> TYPE: DNA
<213> ORGANISM: Homo sapiens
<220> FEATURE:
<221> NAME/KEY: CDS
<222> LOCATION: (60)..(497)
<220> FEATURE:
<221> NAME/KEY: sig_peptide
<222> LOCATION: (60)..(137)
<220> FEATURE:
<221> NAME/KEY: mat_peptide
<222> LOCATION: (138)..(497)

<400> SEQUENCE: 7
```

```
tggtgaggcc cgaggcgttg gagggcttcg cgtctgcttc ggagaccgta aggatattg       59 atg acc atg aga tcc ctg ctc aga acc ccc ttc ctg tgt ggc ctg ctc      107
Met Thr Met Arg Ser Leu Leu Arg Thr Pro Phe Leu Cys Gly Leu Leu
    -25             -20                 -15 tgg gcc ttt tgt gcc cca ggc gcc agg gct gag gag cct gca gcc agc      155
Trp Ala Phe Cys Ala Pro Gly Ala Arg Ala Glu Glu Pro Ala Ala Ser
-10              -5              -1  1               5 ttc tcc caa ccc ggc agc atg ggc ctg gat aag aac aca gtg cac gac      203
Phe Ser Gln Pro Gly Ser Met Gly Leu Asp Lys Asn Thr Val His Asp
                 10                  15                  20 caa gag cat atc atg gag cat cta gaa ggt gtc atc aac aaa cca gag      251
Gln Glu His Ile Met Glu His Leu Glu Gly Val Ile Asn Lys Pro Glu
            25                  30                  35 gcg gag atg tcg cca caa gaa ttg cag ctc cat tac ttc aaa atg cat      299
Ala Glu Met Ser Pro Gln Glu Leu Gln Leu His Tyr Phe Lys Met His
        40                  45                  50 gat tat gat ggc aat aat ttg ctt gat ggc tta gaa ctc tcc aca gcc      347
Asp Tyr Asp Gly Asn Asn Leu Leu Asp Gly Leu Glu Leu Ser Thr Ala
55                  60                  65                  70 atc act cat gtc cat aag gag gaa ggg agt gaa cag gca cca cta atg      395
Ile Thr His Val His Lys Glu Glu Gly Ser Glu Gln Ala Pro Leu Met
                75                  80                  85 agt gaa gat gaa ctg att aac ata ata gat ggt gtt ttg aga gat gat      443
Ser Glu Asp Glu Leu Ile Asn Ile Ile Asp Gly Val Leu Arg Asp Asp
            90                  95                  100 gac aag aac aat gat gga tac att gac tat gct gaa ttt gca aaa tca      491
Asp Lys Asn Asn Asp Gly Tyr Ile Asp Tyr Ala Glu Phe Ala Lys Ser
        105                 110                 115 ctg cag tagatgttat ttggccatct cctggttata tacaaatgtg acccgtgata        547
Leu Gln
    120 atgtgattga acactttagt aatgcaaaat aactcatttc caactactgc tgcagcattt      607 tggtaaaaac ctgtagcgat tcgttacact ggggtgagaa gagataagag aaatgaaaga      667 gaagagaaat gggacatcta atagtcccta agtgctatta ataccttat tggacaagga       727 aaacaacaa aaaaaaatat tagtctgtat taatgctgct gataaagacg tacccaagac       787
```

```
tgggaagaaa aaaaaaaaaa aaaaaaaaaa aaaaa                               823
```

```
<210> SEQ ID NO 8
<211> LENGTH: 146
<212> TYPE: PRT
<213> ORGANISM: Homo sapiens

<400> SEQUENCE: 8

Met Thr Met Arg Ser Leu Leu Arg Thr Pro Phe Leu Cys Gly Leu Leu
    -25              -20              -15
Trp Ala Phe Cys Ala Pro Gly Ala Arg Ala Glu Glu Pro Ala Ala Ser
-10              -5               -1  1               5
Phe Ser Gln Pro Gly Ser Met Gly Leu Asp Lys Asn Thr Val His Asp
                10              15                  20
Gln Glu His Ile Met Glu His Leu Glu Gly Val Ile Asn Lys Pro Glu
            25              30                  35
Ala Glu Met Ser Pro Gln Glu Leu Gln Leu His Tyr Phe Lys Met His
        40              45              50
Asp Tyr Asp Gly Asn Asn Leu Leu Asp Gly Leu Glu Leu Ser Thr Ala
55              60              65                  70
Ile Thr His Val His Lys Glu Glu Gly Ser Glu Gln Ala Pro Leu Met
            75              80              85
Ser Glu Asp Glu Leu Ile Asn Ile Ile Asp Gly Val Leu Arg Asp Asp
            90              95                  100
Asp Lys Asn Asn Asp Gly Tyr Ile Asp Tyr Ala Glu Phe Ala Lys Ser
            105             110             115
Leu Gln
    120
```

```
<210> SEQ ID NO 9
<211> LENGTH: 1815
<212> TYPE: DNA
<213> ORGANISM: Mus musculus

<400> SEQUENCE: 9
gtgcggagaa aagcgtccca gggacggcag ctggcaaggt tcacgttgga gtgcttcgcg    60
actgcgtcgg ggattatcgg ggtacccacc cggaagcatg caaccctac agctgctcag   120
agctcccttg ctgtgtgtcc tgctttgggt cttttgtgct ccaggtgcca gagcccatga   180
ccatggggct gatgtccatc atggcagcgt gggcctggat aagagcacag tgcacgacca   240
agagcacatc atggaacatc tggaaggtgt catcgaccag ccagaggcgg agatgtcccc   300
acaggaactg cagctccatt acttcaaaat gcatgattac gacggcaaca gtttgcttga   360
cggcctagag ctctccatag ccatcactca cgtgcacaag gaggagggga gtgagcaggc   420
gccagtcatg agcgaggatg agctcgtcag catcatagat ggtgtcctga gggacgatga   480
caagaacaat gacggctaca tcgactacgc tgagtttgca aagtcactgc agtagaccgt   540
tggctctttc cttttgtgcac atgtgacccct tgctaatgtg atggacgtgt ctggtaatgc   600
gaaacaactt atttccgtct actgctcagc actttggtaa gagcctgtgg cagtctgtaa   660
gagtgggtg aggaagaagc cacatgactg tggagagaag tgggacaggc ctcagtccct   720
agaggtgtgt ttaagcttgt tgggcaagag ccggatgcgg atcttcggaa gggcggtggg   780
tatcccgagt tctcaggaat ccgactgtag aatgccactc tgacttcttg atgttaatcc   840
atgctaccta agtaaagac aggctgcttg gccaagtgga cacacttgag aaacagtgga   900
```

```
gggagagtgt gaaagccaca cgcttgccct ggttggtcct gtctttaggc agatgtggtc    960
agtattctgt tccccaggca tacagcatca tatattaaag ccacagcaga agaggaatgt   1020
cgcccactga ggccacccag atgcagagtc taggattcct tgcccactgg ccttttggaa   1080
atgaagcacc actggcctga ataattagca ttttccagat cttcagtatc ttccacaact   1140
actgccatac cctgtgttgt atcatttgac caggagggaa accttgaatt ggggtgtgtt   1200
ctctaatcac tttccactgt ctgagctttc ctgacccctg tattgtatcc ttgctcccag   1260
ggctcccttc atggcttgtg aactgttaac ttggtatctc aggttaaact gtcagctggt   1320
ctagcctgag cgaggcctga gaccatcagt cactaagagc agtggctaac ctcatcgaag   1380
ttggaaggaa tgttttttaaa attacctctt cgagcctgaa tacaaagaat aaaagaataa   1440
aagaattctt ttaatttcag ggaagatcag aaaagaaagc ctaaagccct ttagcgttgt   1500
gaacctcagt agtagctgaa agagaagctg ccacaggttg tacttgctct gtgagatgtt   1560
gtagacattc cgtaagagaa tccagaatga tagcaggatc aggaaagaaa tggagccaaa   1620
tctgctctaa ggtgaataga gacttatttt tctttattaa agtattcttg taagacagtt   1680
ttctgtgtca agtatttgtg aaatcagagc tgacatgtaa gctattcttg taatatctca   1740
ttattttgaa agatttatat aatgaactct ggctatctga caataaaatg gatgaaaaag   1800
caaaaaaaaa aaaaa                                                   1815
```

<210> SEQ ID NO 10
<211> LENGTH: 435
<212> TYPE: DNA
<213> ORGANISM: Mus musculus

<400> SEQUENCE: 10

```
atggcaaccc tacagctgct cagagctccc ttgctgtgtg tcctgctttg ggtcttttgt    60
gctccaggtg ccagagccca tgaccatggg gctgatgtcc atcatggcag cgtgggcctg   120
gataagagca cagtgcacga ccaagagcac atcatggaac atctggaagg tgtcatcgac   180
cagccagagg cggagatgtc cccacaggaa ctgcagctcc attacttcaa aatgcatgat   240
tacgacggca acagtttgct tgacggccta gagctctcca tagccatcac tcacgtgcac   300
aaggaggagg ggagtgagca ggcgccagtc atgagcgagg atgagctcgt cagcatcata   360
gatggtgtcc tgagggacga tgacaagaac aatgacggct acatcgacta cgctgagttt   420
gcaaagtcac tgcag                                                   435
```

<210> SEQ ID NO 11
<211> LENGTH: 1815
<212> TYPE: DNA
<213> ORGANISM: Mus musculus
<220> FEATURE:
<221> NAME/KEY: CDS
<222> LOCATION: (98)..(532)
<220> FEATURE:
<221> NAME/KEY: sig_peptide
<222> LOCATION: (98)..(175)
<220> FEATURE:
<221> NAME/KEY: mat_peptide
<222> LOCATION: (176)..(532)

<400> SEQUENCE: 11

```
gtgcggagaa aagcgtccca gggacggcag ctggcaaggt tcacgttgga gtgcttcgcg    60
actgcgtcgg ggattatcgg ggtacccacc cggaagc atg gca acc cta cag ctg    115
                                        Met Ala Thr Leu Gln Leu
                                         -25
```

| | | |
|---|---|---|
| ctc aga gct ccc ttg ctg tgt gtc ctg ctt tgg gtc ttt tgt gct cca<br>Leu Arg Ala Pro Leu Leu Cys Val Leu Leu Trp Val Phe Cys Ala Pro<br>-20                 -15                 -10                 -5 | | 163 |
| ggt gcc aga gcc cat gac cat ggg gct gat gtc cat cat ggc agc gtg<br>Gly Ala Arg Ala His Asp His Gly Ala Asp Val His His Gly Ser Val<br>           -1   1                     5                       10 | | 211 |
| ggc ctg gat aag agc aca gtg cac gac caa gag cac atc atg gaa cat<br>Gly Leu Asp Lys Ser Thr Val His Asp Gln Glu His Ile Met Glu His<br>      15                     20                     25 | | 259 |
| ctg gaa ggt gtc atc gac cag cca gag gcg gag atg tcc cca cag gaa<br>Leu Glu Gly Val Ile Asp Gln Pro Glu Ala Glu Met Ser Pro Gln Glu<br>30                     35                     40 | | 307 |
| ctg cag ctc cat tac ttc aaa atg cat gat tac gac ggc aac agt ttg<br>Leu Gln Leu His Tyr Phe Lys Met His Asp Tyr Asp Gly Asn Ser Leu<br>45                     50                     55                     60 | | 355 |
| ctt gac ggc cta gag ctc tcc ata gcc atc act cac gtg cac aag gag<br>Leu Asp Gly Leu Glu Leu Ser Ile Ala Ile Thr His Val His Lys Glu<br>                65                     70                     75 | | 403 |
| gag ggg agt gag cag gcg cca gtc atg agc gag gat gag ctc gtc agc<br>Glu Gly Ser Glu Gln Ala Pro Val Met Ser Glu Asp Glu Leu Val Ser<br>      80                     85                     90 | | 451 |
| atc ata gat ggt gtc ctg agg gac gat gac aag aac aat gac ggc tac<br>Ile Ile Asp Gly Val Leu Arg Asp Asp Asp Lys Asn Asn Asp Gly Tyr<br>95                     100                105 | | 499 |
| atc gac tac gct gag ttt gca aag tca ctg cag tagaccgttg gctctttcct<br>Ile Asp Tyr Ala Glu Phe Ala Lys Ser Leu Gln<br>     110                    115 | | 552 |
| ttgtgcacat gtgacccttg ctaatgtgat ggacgtgtct ggtaatgcga aacaacttat | | 612 |
| ttccgtctac tgctcagcac tttggtaaga gcctgtggca gtctgtaaga gtggggtgag | | 672 |
| gaagaagcca catgactgtg agagaagtg ggacaggcct cagtccctag aggtgtgttt | | 732 |
| aagcttgttg ggcaagagcc ggatgcggat cttcggaagg gcggtgggta tcccgagttc | | 792 |
| tcaggaatcc gactgtagaa tgccactctg acttcttgat gttaatccat gctacctaaa | | 852 |
| gtaaagacag gctgcttggc caagtggaca cacttgagaa acagtggagg gagagtgtga | | 912 |
| aagccacacg cttgccctgg ttggtcctgt ctttaggcag atgtggtcag tattctgttc | | 972 |
| cccaggcata cagcatcata tattaaagcc acagcagaag aggaatgtcg cccactgagg | | 1032 |
| ccacccagat gcagagtcta ggattccttg cccactggcc ttttggaaat gaagcaccac | | 1092 |
| tggcctgaat aattagcatt ttccagatct tcagtatctt ccacaactac tgccataccc | | 1152 |
| tgtgttgtat catttgacca ggagggaaac cttgaattgg ggtgtgttct ctaatcactt | | 1212 |
| tccactgtct gagctttcct gacccctgta ttgtatcctt gctcccaggg ctcccttcat | | 1272 |
| ggcttgtgaa ctgttaactt ggtatctcag gttaaactgt cagctggtct agcctgagcg | | 1332 |
| aggcctgaga ccatcagtca ctaagagcag tggctaacct catcgaagtt ggaaggaatg | | 1392 |
| ttttttaaaat tacctcttcg agcctgaata caaagaataa agaataaaaa gaattctttt | | 1452 |
| aatttcaggg aagatcagaa aagaaagcct aaagcccttt agcgttgtga acctcagtag | | 1512 |
| tagctgaaag agaagctgcc acaggttgta cttgctctgt gagatgttgt agacattccg | | 1572 |
| taagagaatc cagaatgata gcaggatcag gaaagaaatg gagccaaatc tgctctaagg | | 1632 |
| tgaatagaga cttattttc tttattaaag tattcttgta agacagtttt ctgtgtcaag | | 1692 |
| tatttgtgaa atcagagctg acatgtaagc tattcttgta atatctcatt attttgaaag | | 1752 |
| atttatataa tgaactctgg ctatctgaca ataaaatgga tgaaaagca aaaaaaaaa | | 1812 |
| aaa | | 1815 |

-continued

<210> SEQ ID NO 12
<211> LENGTH: 145
<212> TYPE: PRT
<213> ORGANISM: Mus musculus

<400> SEQUENCE: 12

Met Ala Thr Leu Gln Leu Leu Arg Ala Pro Leu Leu Cys Val Leu Leu
    -25                 -20                 -15

Trp Val Phe Cys Ala Pro Gly Ala Arg Ala His Asp His Gly Ala Asp
-10                  -5                  -1   1               5

Val His His Gly Ser Val Gly Leu Asp Lys Ser Thr Val His Asp Gln
                10                  15                  20

Glu His Ile Met Glu His Leu Glu Gly Val Ile Asp Gln Pro Glu Ala
            25                  30                  35

Glu Met Ser Pro Gln Glu Leu Gln Leu His Tyr Phe Lys Met His Asp
        40                  45                  50

Tyr Asp Gly Asn Ser Leu Leu Asp Gly Leu Glu Leu Ser Ile Ala Ile
55                  60                  65                  70

Thr His Val His Lys Glu Glu Gly Ser Glu Gln Ala Pro Val Met Ser
                75                  80                  85

Glu Asp Glu Leu Val Ser Ile Ile Asp Gly Val Leu Arg Asp Asp Asp
            90                  95                  100

Lys Asn Asn Asp Gly Tyr Ile Asp Tyr Ala Glu Phe Ala Lys Ser Leu
        105                 110                 115

Gln

<210> SEQ ID NO 13
<211> LENGTH: 38
<212> TYPE: DNA
<213> ORGANISM: Rattus rattus
<220> FEATURE:
<221> NAME/KEY: misc_feature
<222> LOCATION: (30)..(30)
<223> OTHER INFORMATION: n = a, c, g or t
<220> FEATURE:
<221> NAME/KEY: misc_feature
<222> LOCATION: (31)..(31)
<223> OTHER INFORMATION: n = a, c, g or t
<220> FEATURE:
<221> NAME/KEY: misc_feature
<222> LOCATION: (32)..(32)
<223> OTHER INFORMATION: n = a, c, g or t
<220> FEATURE:
<221> NAME/KEY: misc_feature
<222> LOCATION: (33)..(33)
<223> OTHER INFORMATION: n = a, c, g or t
<220> FEATURE:
<221> NAME/KEY: misc_feature
<222> LOCATION: (34)..(34)
<223> OTHER INFORMATION: n = a, c, g or t
<220> FEATURE:
<221> NAME/KEY: misc_feature
<222> LOCATION: (35)..(35)
<223> OTHER INFORMATION: n = a, c, g or t
<220> FEATURE:
<221> NAME/KEY: misc_feature
<222> LOCATION: (36)..(36)
<223> OTHER INFORMATION: n = a, c, g or t
<220> FEATURE:
<221> NAME/KEY: misc_feature
<222> LOCATION: (37)..(37)
<223> OTHER INFORMATION: n = a, c, g or t
<220> FEATURE:
<221> NAME/KEY: misc_feature
<222> LOCATION: (38)..(38)
<223> OTHER INFORMATION: n = a, c, g or t

<400> SEQUENCE: 13
tcccgattga attctagacc tgcctcgagn nnnnnnn          38

<210> SEQ ID NO 14
<211> LENGTH: 186
<212> TYPE: PRT
<213> ORGANISM: Caenorhabditis elegans

<400> SEQUENCE: 14

Met Ala Ala Asn Ile Leu Val Val Ser Cys Leu Ile Leu Gly Ser Phe
1               5                   10                  15

Ala His Gln Pro Gln Gln Phe Pro Gly Ser Asn Gln Gln Gln Pro Gln
            20                  25                  30

Gln Gly Gly Gln Ala Glu Gln Ala Gln His Ala Gln Pro Gly Gln Gln
        35                  40                  45

Gln Phe Gly Gly Glu Gln Ala Arg Asp Glu His His Ile Lys Glu His
    50                  55                  60

Leu Asp Gly Lys Val Asp Pro Thr Ala Asn Met Thr Pro Glu Gln Leu
65                  70                  75                  80

Pro Phe His Tyr Phe Asn Met His Asp Leu Asp Lys Asn Gly Lys Leu
                85                  90                  95

Asp Gly Val Glu Leu Ile Lys Ala Ile Thr His Phe His Ala Glu Asn
            100                 105                 110

Pro Gly Pro Gln His Thr Gln Asn Asn Ala Asn Ala Asn His Gln Pro
        115                 120                 125

Pro Pro Leu Pro Ser Glu Val Glu Leu Glu Thr Met Ile Asp Ser Ile
    130                 135                 140

Leu Lys Asp Asp Asp Phe Asn Ala Asp Gly Phe Ile Asp Tyr Gly Glu
145                 150                 155                 160

Phe Leu Lys Ala Gln Lys Leu Arg Glu Asp Gln Ala Arg Ser His Gln
                165                 170                 175

Glu Gln Met Gln Lys Ala Gly Gly Thr Gln
            180                 185

<210> SEQ ID NO 15
<211> LENGTH: 168
<212> TYPE: PRT
<213> ORGANISM: Drosophila melanogaster

<400> SEQUENCE: 15

Met Cys Asn Leu Ser Asn Leu Leu Asn Phe Ile Ile Cys Ile Ala Ser
1               5                   10                  15

Phe Ser Gln Asn Phe Asp Ala Thr Leu Ala Val Lys Arg Gly Pro His
            20                  25                  30

His Pro Arg Gly Glu Thr Arg Arg Val Asp Gln His Leu Thr His Glu
        35                  40                  45

Glu His Arg Ile Asp Asp Leu Lys Asp Met Gly Val Gln Ala Asn
    50                  55                  60

Leu Asp Asp Leu Ser Glu Glu Lys Ile Phe Tyr Met Phe Lys Ala
65                  70                  75                  80

His Asp Asn Asp Asn Asn Ala Leu Asp Gly Leu Glu Met Ile Gln
                85                  90                  95

Ser Ala Met His His Asn Tyr Asp Tyr Phe Lys Asn Asn Glu Arg Asp
            100                 105                 110

Ala Tyr Leu Gln Asn Ala Thr Asp Glu Leu Glu His Phe Ile Glu Ala

```
                115                 120                 125
Ile Asp Lys Phe Leu Leu Ile Ala Asp Asp Asn Asn Asp Gly Leu Leu
    130                 135                 140

His Tyr Pro Glu Phe Val Lys Ala Ile Thr Gly Gly Lys Glu Gln Pro
145                 150                 155                 160

Asn Val Asp Arg Asn Ile Leu Arg
                165

<210> SEQ ID NO 16
<211> LENGTH: 29
<212> TYPE: PRT
<213> ORGANISM: Rattus rattus

<400> SEQUENCE: 16

Glu Phe Lys Glu Ala Phe Ala Leu Phe Asp Lys Asp Gly Asp Gly Thr
1               5                   10                  15

Ile Thr Thr Lys Glu Leu Gly Thr Val Met Arg Ser Leu
            20                  25

<210> SEQ ID NO 17
<211> LENGTH: 29
<212> TYPE: PRT
<213> ORGANISM: Rattus rattus

<400> SEQUENCE: 17

Glu Leu Gln Asp Met Ile Asn Glu Val Asp Ala Asp Gly Asn Gly Thr
1               5                   10                  15

Ile Asp Phe Pro Glu Phe Leu Ser Leu Met Ala Arg Lys
            20                  25

<210> SEQ ID NO 18
<211> LENGTH: 29
<212> TYPE: PRT
<213> ORGANISM: Rattus rattus

<400> SEQUENCE: 18

Glu Leu Ile Glu Ala Phe Lys Val Phe Asp Arg Asp Gly Asn Gly Leu
1               5                   10                  15

Ile Ser Ala Ala Glu Leu Arg His Val Met Thr Asn Leu
            20                  25

<210> SEQ ID NO 19
<211> LENGTH: 29
<212> TYPE: PRT
<213> ORGANISM: Rattus rattus

<400> SEQUENCE: 19

Glu Val Asp Glu Met Ile Arg Glu Ala Asp Ile Asp Gly Asp Gly His
1               5                   10                  15

Ile Asn Tyr Glu Glu Phe Val Arg Met Met Val Ala Lys
            20                  25

<210> SEQ ID NO 20
<211> LENGTH: 12
<212> TYPE: PRT
<213> ORGANISM: Artificial Sequence
<220> FEATURE:
<223> OTHER INFORMATION: Loop consensus sequence
<220> FEATURE:
<221> NAME/KEY: MISC_FEATURE
<222> LOCATION: (2)..(2)
<223> OTHER INFORMATION: X = any amino acid
<220> FEATURE:
```

```
-continued

<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid
<220> FEATURE:
<221> NAME/KEY: MISC_FEATURE
<222> LOCATION: (11)..(11)
<223> OTHER INFORMATION: X = any amino acid

<400> SEQUENCE: 20

Asp Xaa Asp Gly Asp Gly Xaa Ile Asp Xaa Xaa Glu
1               5                   10
```

HUMAN AND MAMMALIAN STEM CELL-DERIVED NEURON SURVIVAL FACTORS

TECHNICAL FIELD

The present invention relates to human, rat and mouse Stem cell-Derived Neuron Survival Factors (hereinafter, simply referred to as "SDNSF"). In more detail, it relates to human, rat and mouse SDNSF, a process for producing them, cDNA encoding SDNSF, a vector comprising the cDNA, host cells transformed by the vector, an antibody against SDNSF, a pharmaceutical compositions containing SDNSF or the antibody, a method of assaying SDNSF, a reagent for assaying SDNSF, and a screening method using SDNSF.

BACKGROUND ART

In adult brain, it is a long established theory that a new neuron is not generated, and that in an injury to the central nerve system caused by brain infarction, brain hemorrhage, spinal cord injury, etc. and in a neurodegenerative disease such as Parkinson's disease and amyotrophic lateral sclerosis (ALS), recovery of the function which the movement was lost according to the cell death of a neuron was difficult. In recent years, however, it was shown that a neuron was newly generated in adult brain (hippocampus, cerebral cortex association area, lateral cerebral ventricle) of higher mammals such as human and monkey, and that a new neuron in these regions was generated from a neuronal stem cell. It was also demonstrated that a neuronal stem cell existed in aged people's brain and it could differentiate into a neuron. These facts suggest that cerebral regenerative medical treatment is not limited to cell therapy which transplants cells, but therapy which activates inherent neuronal stem cells directly by adminstrating a drug medicine containing protein or compound or by gene therapy technology is possible.

In order to obtain a specific polypeptide or a cDNA encoding it, there have been generally employed methods comprising confirming the target biological activity in a tissue or a cell culture medium and then cloning of a gene through the isolation and purification of a polypeptide and further methods comprising expression-cloning of a gene with the guidance of the biological activity. However, it is frequently observed that a gene, which has been cloned with the guidance of a certain activity, codes for a known polypeptide since many physiologically active polypeptides occurring in vivo have various biological activities. Further, most intravital physiologically active factors are generated only in a trace amount or under a specific physiological condition, which makes the isolation and purification thereof and the confirmation of biological activity difficult.

DISCLOSURE OF THE INVENTION

The inventors focused on novel factors (polypeptides), especially secretory proteins and membrane proteins which have secretion signals, useful for the medical treatment or diagnosis of an injury to the central nerve system or a neurodegenerative disease, diagnosis or research of a brain tumor, and examined repeatedly and wholeheartedly. Consequently, the inventors have isolated the novel polypeptide molecule concerning a neuronal stem cell, and found out that it is available for regenerative medical treatment abovementioned and for specific marker of a neuron.

The present inventors have studied the cloning of genes for proliferation and differentiation factors in hemetopoietic and immune systems. They have paid attention to the fact that most secretory proteins such as proliferation and/or differentiation factors (for example various cytokines) and membrane proteins such as receptors thereof (hereinafter these proteins will be referred to generally as secretory proteins and the like) have sequences called signal peptides in the N-termini. Extensive studies have been conducted to provide a process for efficiently and selectively cloning genes encoding signal peptides. As a result, a process (signal sequence trap (SST) method) has been devised using animal cells whereby the existence of a signal peptide can be easily examined (Japanese Patent No. 2,879,303). Furthermore, a process (the yeast SST method) for massively and easily isolating genes encoding signal peptides by using yeast was also developed based on the same concept (U.S. Pat. No. 5,536,637).

By using this method, the inventors have identified successfully a novel secretory protein which is generated by neural stem cells derived from adult rat hippocampus and a cDNA encoding the protein, and found out a full-length cDNA from neural stem cells derived from adult rat hippocampus based on the information.

The inventors have confirmed that the polypeptide had survival supporting activity to some cerebral neurons (primary cultured cells from hippocampus nerve and stem cells derived from hippocampus), as might be explained in detail behind, and completed the invention. The polypeptide is the useful factor as which the function was specified.

The cDNA sequence which this invention offers was identified as a rat SDNSF clone shown in SEQ ID No. 1 or 2, and isolated from cDNA library prepared from stem cells derived from hippocampus based on the information obtained by yeast SST method. The rat SDNSF clone shown in SEQ ID No. 1 is a full-length cDNA encoding the secretory protein (it is indicated as rat SDNSF protein in the invention).

The cDNA sequence which this invention offers was identified as a human SDNSF clone shown in SEQ ID No. 5 or 6, and isolated from cDNA library prepared from stem cells derived from hippocampus based on the information obtained by yeast SST method. The human SDNSF clone shown in SEQ ID No. 5 is a full-length cDNA encoding the secretory protein (it is indicated as human SDNSF protein in the invention).

The cDNA sequence which this invention offers was identified as a mouse SDNSF clone shown in SEQ ID No. 9 or 10, and isolated from cDNA library prepared from stem cells derived from hippocampus based on the information obtained by yeast SST method. The mouse SDNSF clone shown in SEQ ID No. 9 is a full-length cDNA encoding the secretory protein (it is indicated as mouse SDNSF protein in the invention).

The nucleotide sequence encoding rat SDNSF was compared with sequences in GenBank and NCBI utilizing the programs BLASTN, FASTA and UNIGENE, and the amino acid sequence of rat SDNSF was compared with sequences utilizing the programs BLASTP, Fly Database and SwisProt, to reveal no identical sequence. From the results, it became clear that the polypeptide of the invention was a novel secretory protein.

From the facts that the polypeptide of the invention has sustentation activity on neuron in a portion of brain, has EF hand motifs in spite of secretory protein, is a possible cytokine which is regulated by extracellular calcium or calcium from organelle involved in secretory pathway, and has no sequence homology to known neurotrophins, it is thought that the polypeptide is a cytokine which promotes formation or support of survival of neurons other than sympathetic nerve, sensory nerve, neuron in spinal cord motor nerve nucleus and cholinergic nerve in basal ganglia which are known to be neurotrophin dependence by the analysis using deficit mouse of known neurotrophin gene, and that the polypeptide leads to elucidate etiologies of neurodegenerative diseases and to treat them.

The present invention relates to:

(1) A substantially purified form of a polypeptide comprising the amino acid sequence shown in SEQ ID NO. 4, 8 or 12, a homologue thereof, a fragment thereof or a homologue of the fragment, (2) The polypeptide according to (1) that comprises the amino acid sequence shown in SEQ ID NO. 4, 8 or 12, (3) A cDNA encoding the polypeptide according to (1) or (2), (4) The cDNA according to (3), comprising the nucleotide sequence shown in SEQ ID NO. 1, 2, 5, 6, 9 or 10, or a fragment selectively hybridized to the sequence, (5) A replication or expression vector comprising the cDNA according to (3) or (4), (6) A host cell transformed with the replication or expression vector according to (5), (7) A process for producing the polypeptide according to (1) or (2), which comprises culturing the host cell according to (6) under a condition effective to express the polypeptide according to (1) or (2), (8) A monoclonal or polyclonal antibody against the polypeptide according to (1) or (2), (9) A pharmaceutical composition containing the polypeptide according to (1) or (2) or the antibody according to (8), in association with a pharmaceutically acceptable excipient and/or carrier,

(10) A pharmaceutical composition effective for the medical treatment of a neurodegenerative disease, containing the polypeptide according to (1) or (2) or the antibody according to (8), in association with a pharmaceutically acceptable excipient and/or carrier,

(11) The pharmaceutical composition according to (10), in which the neurodegenerative disease is an injury to the central nerve system by brain infarction, brain hemorrhage, spinal cord injury, etc.,

(12) A method for measuring the polypeptide according to (1) or (2),

(13) An immunochemical method for measuring the polypeptide according to (1) or (2), comprising using the antibody according to (8),

(14) A reagent for detecting the polypeptide according to (1) or (2), comprising using the method according to (12) or (13),

(15) A reagent for testing tumor, comprising using the method according to (12) or (13),

(16) The reagent according to (14), in which the tumor is a brain tumor,

(17) A method for screening a compound having agonistic or antagonistic activity against the polypeptide, comprising using the polypeptide according to (1) or (2),

(18) An agent for the treatment of an injury to the central nerve system which comprises, as an active ingredient, the polypeptide according to (1) or (2),

(19) The reagent according to (19), in which the injury to the central nerve system is the one caused by a brain infarction,

(20) The reagent according to (19), in which the injury to the central nerve system is the one caused by a brain hemorrhage, and

(21) The reagent according to (19), in which the injury to the central nerve system is the one caused by a spinal cord injury.

DETAILED DESCRIPTION

A polypeptide of SEQ ID NO. 4, 8 or 12 in substantially purified form will generally comprise the polypeptide in a preparation in which more than 90%, eg. 95%, 98% or 99% of the polypeptide in the preparation is that of the SEQ ID NO. 4, 8 or 12.

A polypeptide homologue of the SEQ ID NO. 4, 8 or 12 will be at least 70%, preferably at least 80% or 90%, and more preferably 95% homologous to the polypeptide over a region of at least 20, preferably at least 30 for instance 40, 60, 80 or 100 contiguous amino acids. Such polypeptide homologues will be referred to below as a polypeptide according to the invention.

Furthermore, fragments of SEQ ID NO. 4, 8 or 12 or its homologues will be at least 10, preferably at least 15 for example 20, 25, 30, 40, 50 or 60 amino acids in length of the polypeptide.

A cDNA capable of selectively hybridizing to the cDNA of SEQ ID NO. 1, 2, 5, 6, 9 or 10 will be generally at least 70%, preferably at least 80% or 90%, and more preferably at least 95% homologous to the cDNA of SEQ ID NO. 1, 2, 5, 6, 9 or 10 over a region of at least 20, preferably at least 30, for instance 40, 60, 80 or 100 contiguous nucleotides. Such cDNA will be encompassed by the term "cDNA according to the invention".

Fragments of SEQ ID NO. 1, 2, 5, 6, 9 or 10 will be at least 10, preferably at least 15 for example 20, 25, 30 or 40 nucleotides in length of the cDNA. Such fragments will be encompassed by the term "cDNA according to the invention".

Because SDNSF protein of the invention is secreted in great quantities from undifferentiated neuroblastoma and glioblastoma among brain tumors, but not secreted from differentiated glioma, and there is no available neural tumor marker secreted in circulating blood or spinal fluid, SDNSF protein could be the first marker for undifferentiated neural tumor of which detection is possible in blood.

A further embodiment of the invention provides replication and expression vectors comprising cDNA according to the invention. The vectors may be, for example, plasmid, virus or phage vectors provided with an origin of replication, optionally a promoter for the expression of the said DNA and optionally a regulator of the promoter. The vector may contain one or more selectable marker genes, for example an ampicillin resistance gene. The vector may be used in vitro, for example for the production of RNA corresponding to the cDNA, or used to transform a host cell.

A further embodiment of the invention provides host cells transformed or transfected with the vectors for the replication and expression of cDNA according to the invention, including the cDNA of SEQ ID NO. 1, 2, 5, 6, 9 or 10 or the open reading frame thereof. The cells will be chosen to be compatible with the vector and may for example be bacterial, yeast, insect or mammalian.

A further embodiment of the invention provides a method of producing a polypeptide which comprises culturing host cells of the present invention under conditions effective to express a polypeptide of the invention. Preferably, cultivation is carried out under conditions in which the polypeptide of the invention is expressed and then generated from the host cells.

A cDNA according to the invention may also be inserted into the vectors described above in an antisense orientation in order to provide for the production of antisense RNA. Such antisense RNA may be used in a method of controlling the levels of a polypeptide of the invention in a cell.

An embodiment of the invention also provides monoclonal or polyclonal antibodies against a polypeptide of the present invention. A further embodiment of the invention provides a process for production of monoclonal or polyclonal antibodies to the polypeptides of the present invention. Monoclonal antibodies may be prepared by common hybridoma technology using polypeptides of the present invention or fragments thereof as an immunogen. Polyclonal antibodies may also be prepared by common means which comprises inoculating host animals, for example a rat or a rabbit, with polypeptides of the invention and recovering immune serum.

An embodiment of the invention also provides pharmaceutical compositions containing a polypeptide of the present invention, or an antibody against the polypeptide, in association with a pharmaceutically acceptable excipient and/or carrier.

(A) As the polypeptide of the present invention referred to above 1, those which have deficiency in a part of their amino acid sequence (e.g., a mature polypeptide consisted of the only essential sequence for revealing a biological activity in an amino acid sequence shown in SEQ ID NO. 4), those which have a part of their amino acid sequence replaced by other amino acids (e.g., those replaced by an amino acid having a similar property) and those which have other amino acids added or inserted into a part of their amino acid sequence, as well as those comprising the amino acid sequence shown in SEQ ID NO. 4, 8 or 12.

As known well, there are one to six kinds of codon encoding one amino acid (for example, one kind of codon for Methionine, and six kinds of codon for leucine are known). Accordingly, the nucleotide sequence of cDNA can be changed without changing the amino acid sequence of the polypeptide.

(B) The cDNA of the present invention referred to above 3 includes every group of nucleotide sequences encoding polypeptides of SEQ ID NO. 4, 8 or 12 shown in (A). There is a probability that yield of a polypeptide is improved by changing a nucleotide sequence.

(C) The cDNA specified in SEQ ID NO. 2, 6 or 10 is an embodiment of the cDNA shown in (B), and indicates the sequence of natural form.

(D) The cDNA shown in SEQ ID NO. 1, 5 or 9 indicates the sequence in which natural non-coding region is added to the cDNA specified in (C).

A cDNA carrying nucleotide sequence shown in SEQ ID NO. 1, 5 or 9 is prepared by the following method.

First, Yeast SST method (see U.S. Pat. No. 5,536,637) is briefly described below.

Yeast such as *Saccharomyces cerevisiae* should secrete invertase into the medium in order to take sucrose or raffinose as a source of energy or carbon (Invertase is an enzyme to cleave raffinose into sucrose and melibiose, sucrose into fructose and glucose.). It is known that many of known mammalian signal sequences make yeast secrete its invertase.

From this knowledge, SST method was developed as a screening method to find a novel signal peptide which enables invertase secretion of yeast from mammalian cDNA library with growth of the yeast on raffinose medium as an index.

Non-secretory type invertase gene SUC2 (GENBANK Accession No. V 01311) lacking initiation codon ATG was inserted to yeast expression vector to prepare yeast SST vector pSUC2. In this expression vector, ADH promoter, ADH terminator (both were derived from AAH5 plasmid (Gammerer, Methods in Enzymol. 101, 192-201, 1983)), 2μ ori (as a yeast replication origin), TRP1 (as a yeast selective marker), ColE1 ori (as a *E. Coli* replication origin) and ampicillin resistance gene (as a drug resistance marker) were inserted. Mammalian cDNA was inserted into the upstream of SUC2 gene to prepare yeast SST cDNA library. Yeast lacking secretory type invertase, was transformed with this library.

If inserted mammalian cDNA encodes a signal peptide, the yeast could survive on raffinose medium as a result of restoring secretion of invertase. By culturing yeast in colonies to prepare plasmids and determine the nucleotide sequence of the insert cDNAs, it is possible to identify novel signal peptide rapidly and easily.

Preparation of yeast SST cDNA library is as follows:

(1) mRNA is isolated from targeted cells, a double-strand cDNA is synthesized by using random primer with certain restriction enzyme (enzyme I) recognition site, (2) the double-strand cDNA is ligated to adapter containing certain restriction endonuclease (enzyme II) recognition site different from enzyme I, digested with enzyme I and fractionated in a appropriate size, (3) the obtained cDNA fragment is inserted into yeast expression vector on the upstream region of invertase gene of which signal peptide is deleted and the library is transformed.

Detailed description of each step is as follows:

In step (1), mRNA is isolated from mammalian organs or cell lines after stimulating them with appropriate stimulator if necessary by known methods (as described in Molecular Cloning (Sambrook, J., Fritsch, E. F. and Maniatis, T., Cold Spring Harbor Laboratory Press, 1989) or Current Protocol in Molecular Biology (F. M. Ausubel et al, John Wiley & Sons, Inc.) unless otherwise specified).

A suitable tissue may be heart of fetal mouse. Double-strand cDNA synthesis using random primer is performed by known methods.

Any sites may be used as restriction endonuclease recognition site I which is linked to adapter and restriction endonuclease recognition site II which is used in step (2), insofar as both sites are different each other. Preferably, XhoI is used as enzyme I and EcoRI as enzyme II.

In step (2), ends of cDNA are blunted with T4 DNA polymerase, and ligated to enzyme II adapter and digested with enzyme I. Fragment cDNA is analyzed with agarose-gel electrophoresis (AGE) and cDNA fraction ranging in size from 300 to 800 bp is selected. As mentioned above, any enzyme may be used as enzyme II insofar as it is not same with the enzyme I.

In step (3), cDNA fragment obtained in step (2) is inserted into yeast expression vector on the upstream region of invertase gene of which signal peptide is deleted. *E. coli* is transformed with the expression vector. Many vectors are known as yeast expression plasmid vector. For example, YEp24 is also functioned in *E. Coli*. Preferably pSUC2 as described above is used.

Many host *E. Coli* strains are known as usable for transformation, preferably DH10B competent cell is used. Any known transformation method is available, preferably it is performed by electropolation method. Transformant is cultured by conventional methods to obtain cDNA library for yeast SST method.

However, not all of the cloned cDNA fragments are introduced into this cDNA library. Further, not all of the gene fragments encode unknown (novel) signal peptides. It is therefore necessary to screen a gene fragment encoding for an unknown signal peptide from the library.

Therefore, screening of fragments containing a sequence encoding an appropriate signal peptide is performed by transformation of the cDNA library into *Saccharomyces cerevisiae* (e.g. YT455 strain) lacking the invertase gene or strain which artificially lack the gene (it may be prepared by known methods.). Transformation of yeast is performed by known methods, e.g. lithium acetate method. Transformant is cultured in a selective medium, then transferred to a medium containing raffinose as a carbon source. Survival colonies are selected and then plasmid is collected. Survival colonies on a raffinose-medium indicates that some signal peptide of secretory protein was inserted to this clone.

With respect to isolated positive clones, the nucleotide is determined. As to a cDNA encoding unknown protein, full-length clone may be isolated by using cDNA fragment as a probe, and then the full-length nucleotide sequence is determined. The manipulation is performed by known methods.

Once the nucleotide sequences shown in SEQ ID NO. 1, 5 or 9 are determined partially or preferably fully, it is possible to obtain cDNA encoding mammalian protein itself, homologue or subset. By screening cDNA library or mRNA derived from mammals by PCR method with any synthesized oligonucleotide primers or by hybridization with any fragment as a probe, it is possible to obtain cDNA encoding other mammalian homologue protein from other mammalian cDNA or genome library.

If the cDNA obtained above contains a nucleotide sequence of cDNA fragment obtained by SST (or homologous sequence thereof), it implies that the cDNA encodes signal peptide. Accordingly, it is clear that the length of the cDNA is full or almost full. (All signal sequences exist at N-termini of a protein and are encoded at 5'-termini of open reading frame of cDNA.)

By known methods, the confirmation of full-length may be carried out by Northern analysis with the said cDNA as a probe. The cDNA is assumed to have almost complete length if the length of the cDNA is almost the same with the length of the mRNA obtained in the hybridizing band.

The present invention provides both types of protein, i.e., full-length and mature. The full-length proteins are specified with the amino acid sequences translated from the nucleotides shown in SEQ ID NO. 4, 8 or 12. The mature proteins are obtained by expression in suitable mammal cells or other host cells transformed by the full-length DNA shown in SEQ ID NO. 1, 5 or 9. Sequences of mature proteins could be predicted from full-length amino acid sequences.

Once the nucleotide sequences shown in SEQ ID No. 1, 2, 5, 6, 9 or 10 are determined, cDNAs of the present invention are obtained by chemical synthesis, or by hybridization making use of nucleotide fragments which are chemically synthesized as a probe. Furthermore, cDNAs of the invention are obtained in desired amount by transforming a vector that contains the DNA into a proper host, and culturing the transformant.

The polypeptides of the present invention may be prepared by:
(1) isolating and purifying from an organism or a cultured cell,
(2) chemically synthesizing, or
(3) using recombinant DNA technology, preferably, by the method described in (3) in an industrial production.

Examples of expression system (host-vector system) for producing a polypeptide by using recombinant DNA technology are the expression systems of bacteria, yeast, insect cells and mammalian cells.

In the expression of the polypeptide, for example, in *E. Coli*, the expression vector is prepared by adding the initiation codon (ATG) to 5' end of a cDNA encoding mature peptide, connecting the cDNA thus obtained to the downstream of a proper promoter (e.g., trp promoter, lac promoter, λ PL promoter, and T7 promoter), and then inserting it into a vector (e.g., pBR322, pUC18 and pUC19) which functions in an *E. coli* strain.

Then, an *E. coli* strain (e.g., *E. coli* DH1 strain, *E. coli* JM109 strain and *E. coli* HB101 strain) which is transformed with the expression vector described above may be cultured in an appropriate medium to obtain the desired polypeptide. When a signal peptide of bacteria (e.g., signal peptide of pel B) is utilized, the desired polypeptide may be also released in periplasm. Furthermore, a fusion protein with other polypeptide may also be produced.

In the expression of the polypeptide, for example, in mammalian cells, for example, the expression vector is prepared by inserting the DNA encoding nucleotide shown in SEQ ID NO 1, 2, 5, 6, 9 or 10 into the downstream of a proper promoter (e.g., SV40 promoter, LTR promoter and metallothionein promoter) in a proper vector (e.g., retrovirus vector, papilloma virus vector, vaccinia virus vector and SV40 vector). A proper mammalian cell (e.g., monkey COS-1 cell, COS-7 cell, Chinese hamster CHO cell, mouse L cell etc.) is transformed with the expression vector thus obtained, and then the transformant is cultured in a proper medium, the secretory protein of the present invention can be secreted into the culture medium as the aimed polypeptide. Then, by linking to cDNA fragment coding other polypeptides, for example, common region (Fc portion) of antibody, fusion proteins can be produced. Polypeptides obtained by the method above can be isolated and purified by conventional biochemical methods.

INDUSTRIAL APPLICABILITY

A polypeptide and cDNA encoding it of the invention are thought to have one or more effects or biological activities (The effects or biological activities relevant to assay enumerated below are included).

Administration or use of the protein or of cDNA coding the protein (for example, gene therapy (including regenerative therapy) or vectors suitable for cDNA transfection) may provide the effect or biological activities described about the protein of the invention.

The polypeptide of the invention has sustentation activity on neuron in a portion of brain (primary cultured cells from hippocampus nerve and stem cells derived from hippocampus) and, therefore, is efficacious in treating neurodegenerative disease (injury in the central nerve system by brain infarction, brain hemorrhage, spinal cord injury, etc.).

Quantitative analysis of the polypeptide of the present invention in vivo can be performed using polyclonal or monoclonal antibodies against the polypeptide of the present invention. It can be used in studies on relationship between this polypeptide and disease, or diagnosis of disease, etc. The polyclonal and the monoclonal antibodies can be prepared using this polypeptide or its fragment as an antigen by conventional methods.

Identification, purification or gene cloning of known or unknown proteins (ligands) which are connected with the polypeptide of the present invention can be performed using the polypeptide of the present invention by, for example, preparation of the affinity-column.

Identification of molecules which interact with the polypeptide, molecular cloning of the gene may be conducted, for example, by west-western blot, using the polypeptide, or by yeast two-hybrid method, using the cDNA (desirably cDNA coding the polypeptide).

Screening, which can identify agonists or antagonists against the polypeptide receptor and inhibitors against interaction between receptors and signal transduction molecules can be performed by using the polypeptide.

For example, the screening could be performed by the following steps:

(a) The polypeptide of the invention, compound to be screened and reaction mixture including cells are mixed (the reaction mixture includes markers which are transferred into cells as the cell grows and peptides except for the polypeptide for efficient observation of the function of the polypeptide.) under condition which the cells are normally stimulated by the polypeptide, then, (b) It is determined whether the compound is a useful agonist or antagonist by measuring the cell growth.

The cDNA of the invention may be useful not only as an important and essential template in production of the polypeptide of the present invention which is expected to have a considerable utility, but also for diagnoses and treatments of hereditary diseases (treatments of gene deficiency or treatments which anti-sense DNA (RNA)s intercept expression of polypeptides, etc). In addition, genomic DNAs may be isolated by using cDNA of the invention as a probe.

For the usage for above mentioned diseases, administration of the polypeptide of the invention or the antibodies against the polypeptide of the invention can be carried out in systemic or local, generally peroral or parenteral ways. Oral, intravenous and intracerebroventricular administration are preferred.

The dosage to be administered depends upon age, body weight, symptom, desired therapeutic effect, route of administration, and duration of the treatment etc. In human adults, one dose per person is generally between 100 μg and 100 mg by oral administration up to several times per day, or between 10 μg and 100 mg by parenteral administration up to several times per day.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, or as injections, liniments or suppositories etc. for parenteral administration.

Examples of solid compositions for oral administration include compressed tablets, pills, capsules, dispersible powders and granules etc. Examples of capsules include hard capsules and soft capsules.

In such solid compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration may contain pharmaceutically-acceptable emulsions, solutions, suspensions, syrups and elixirs, and also may contain inert qjdiluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents such as sodium sulfite etc., stabilizing agents providing for isotonic behavior, isotonic buffer (sodium chloride, sodium citrate, citric acid, etc.). For preparation of such spray compositions, for example, the methods described in the U.S. Pat. Nos. 2,868,691 and 3,095,355 may be used.

Injections for parenteral administration include sterile aqueous or non-aqueous solutions, suspensions and emulsions. In aqueous or non-aqueous solutions or suspensions, one or more active compound(s) is or are admixed with at least one inert diluent (s). Aqueous diluents may be distilled water for injection, physiological salt solution, etc. Inert non-aqueous diluents (s) may be propylene glycol, polyethylene glycol, oil of the plant such as olive oil, alcohol such as ethanol, POLYSOLBATE 80™, etc.

Such compositions may comprise additional preserving agents, wetting agents, emulsifying agents, dispersing agents, stabilizing agent (such as human serum albumin, lactose, etc.), and assisting agents such as assisting agents for dissolving (arginine, asparaginic acid, etc.)

BRIEF DESCRIPTION OF THE DRAWINGS

FIG. 1 (A) shows an alignment of deduced amino acid sequences of human (hSDNSF; SEQ ID NO: 8), mouse (mSDNSF; SEQ ID NO: 12), and rat SDNSF (rSDNSF; SEQ ID NO: 4), along with a *Drosophila* protein (NP_505967; SEQ ID NO: 14) and a Nematode protein (CG12817; SEQ ID NO: 15), (B) existence of two EF hand motifs (calcium binding motif) in the downstream of the signal peptide, FIG. 2 shows the EF hand motifs of SDNSF (rSDNSF 1=amino acids 71-96 of SEQ ID NO: 4: rSDNSF 2=amino acids 121-145 of SEQ ID NO: 4) and those of calmodulin (calmodulin 1=SEQ ID NO: 16; calmodulin 2=SEQ ID NO: 17; calmodulin 3=SEQ ID NO: 18; calmodulin 4=SEQ ID NO: 19), calcium secretory protein, have common sequences (consensus EF=SEQ ID NO: 20)

BEST MODE FOR CARRYING OUT THE INVENTION

Figure 3:
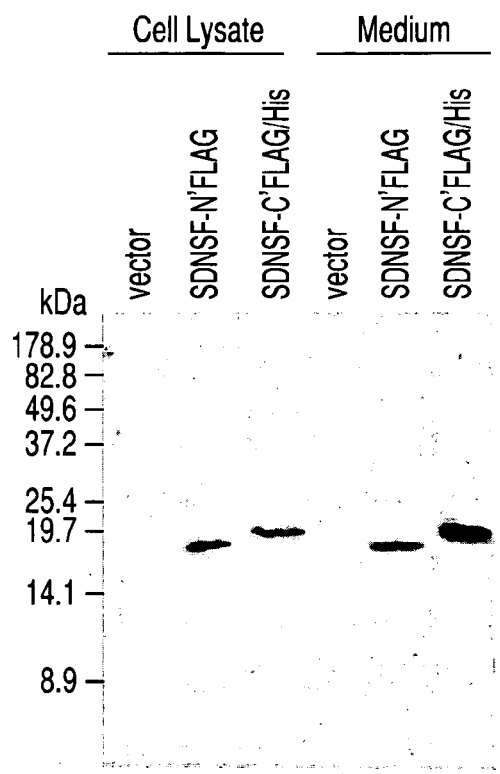
FIG. 3 is the result of Western Blot analysis with anti-SDNSF antibody and anti-FLAG antibody, showing SDNSF protein is secreted into the culture medium.

The present invention is more specifically explained by means of the following examples regarding SDNSF, but is not limited only to these examples.

Example 1

Preparation of Poly(A)$^+$ RNA

Total RNA was extracted from PZ5 cells, which was cloned from neural stem cells derived from adult rat hippocampus, with TRI$_{zol}$ reagent™ (purchased from Life Technologies, Inc), and poly(A)$^+$ RNA was purified with Oligotex-dT30<Super>™ (purchased from Roche).

Example 2

Construction of Yeast SST cDNA Library

Double-stranded cDNA was synthesized from above-described poly(A)$^+$ RNA with a primer, in which XhoI site 9 mer was connected with,

5'-TCC CGA TTG AAT TCT AGA CCT GCC TCG AGN NNN NNN NN-3' (SEQ ID NO. 13)

by using Super Script Choice System™ (purchased from Life Technologies, Inc). It was connected with EcoRI adaptor (purchased from GIBCOERL) by using DNA ligation kit Ver.2™ (purchased from TAKARA SYUZO, hereinafter this kit was used for ligation of cDNA), digested with XhoI, electrophoresed in agarose gel and 400-800 bp cDNAs were cut off from the gel. The cDNAs were inserted into EcoRI/XhoI site of pSuc2t7lori (see U.S. Pat. No. 5,536,637), introduced into *E. coli* DH10 by electropolation to obtain cDNA library for yeast SST method.

Example 3

Screening by SST and Sequencing of Positive Clones

Plasmids were prepared from the cDNA library, yeast YTK12 was transformed with the plasmids by lithium acetate method (see Current Protocols in Molecular Biology 13.7.1) and plated onto selection medium for yeast transformants (CMO-Trp medium) lacking tryptophan. After 48 hours incubation at 30° C., colonies (transformants) were replicated onto YPR plates, of which carbon source is raffinose, by using Accutran Replica Plater™ (purchased from Schleicher & Schuell) and incubated for 14 days at 30° C.

On day 3 or later, each yeast colony was purified by streaking onto YPR plates and incubated for 48 hours at 30° C. Single colony was inoculated into YPD medium and incubated for further 48 hours at 30° C., then plasmid was prepared. PCR reaction was performed with two kinds of primers having the sequences at the ends of pSUC2 cloning site (primer for sense-strand is biotin-labelled) by known method to amplify insert cDNA, biotin-labelled single-stranded cDNA was purified using Dynabeads™ (purchased from DYNAL) and then sequenced by cycle-sequencing method using fluorescence-dye terminator with DNA Sequencing kit (Dye Terminator Cycle Sequencing Ready Reaction™) (purchased from Applied Biosystems Inc.). DNA sequencer 373 (Applied Biosystems Inc.) was used for reading the nucleotide sequence (hereinafter sequencing was carried out by this method).

DNA sequences thus obtained and deduced amino acid sequences were compared with sequences in data bases, it became clear that a clone named SDNSF was a novel cDNA. Therefore, full-length cDNA cloning was tried with this fragment cDNA of SDNSF clone (hereinafter referred to as "SDNSF SST fragment cDNA"). A comparison of the deduced amino acid sequence with those of known signal peptides indicated that SDNSF SST fragment cDNA had signal peptide both functionally and structurally.

Example 4

Full-Length cDNA Cloning and Sequencing

One million plaques obtained from PZ5 cDNA library were transferred to nylon membrane. Hybridization was carried out with $32^P$-labelled rat SDNSF SST fragment cDNA as a probe by known method to obtain many positive clones. One clone among them was isolated, introduced into E. coli DH5α, and its plasmid was prepared. After sequencing of 5' region of the insert and confirming the DNA contained the sequence of rat SDNSF SST fragment cDNA, full length sequencing was performed to obtain the sequence shown in SEQ ID No. 1. The open reading frame was also determined to obtain the translated amino acid sequence shown in SEQ ID No. 2 and the deduced amino acid sequence shown in SEQ ID No. 4.

The amino acid sequence and nucleotide sequence encoding the polypeptide of the invention (referred to as rat SDNSF polypeptide) were compared with sequences in NCBI data base to reveal no identical sequence. Furthermore, it became clear that rat SDNSF polypeptide had no transmembrane region and that rat SDNSF polypeptide was a novel secretory protein.

The result of motif search revealed that SDNSF had a signal peptide and two EF hand motifs (calcium binding motif) downstream of the signal peptide (FIG. 1). EF hand motif of SDNSF and that of calmodulin, a calcium secretory protein, have common sequences (FIG. 2). It is rare that a secretory protein has the EF hand motif, however, it is reported that BM-40 and its related proteins have a similar structure. The EF hands in BM-40 is suspected to be involved in the conformation change of the protein depending on the concentration of calcium in vesicle and secretion efficiency of BM-40 (Literature 1: Busch E et. al., Calcium affinity cooperativity and domain interaction of extracellular EF-hands present in BM-40, J. Biol. Chem., 275(33), 25508-15(2000)).

Example 5

Sequencing of Human and Mouse SDNSF Genes

Homology searches on mammalian ESTs and UNIGENE DNA data bases revealed human and mouse ESTs homologous to rat SDNSF.

Consequently, the inventors isolated full length human and mouse SDNSF genes using the sequence information by known method and sequenced completely to obtain the nucleotide sequence's shown in SEQ ID No. 5 and 9, respectively. The open reading frame was also determined to obtain the deduced amino acid sequence shown in SEQ ID No. 8 and 12, respectively. It was revealed from above information that said human and mouse clones were full length and their amino acid sequences were 87% and 90% identical to that of rat SDNSF, respectively.

The nucleotide sequences and amino acid sequences of the human and mouse SDNSF were compared with sequences on nucleotide and amino acid data bases to reveal no identical sequence as was the case with rat SDNSF. From this, it became clear that the polypeptides of the invention were novel secretory proteins as well.

Example 6

Homology Searches on Data Bases for Non-Mammals

Homology searches on nematode and *drosophila* data bases revealed that F55A11.1, which had been reported to be a virtual protein of nematode, and CG12817, which had been reported to be a gene product of *drosophila*, had 20 to 30% identities in amino acid sequence with the polypeptides. These data base searches suggest that SDNSF genes are highly conserved.

Example 7

Preparation of Anti-SDNSF Polyclonal Antibody

Three kinds of rat SDNSF partial polypeptides were synthesized by solid-phase method and conjugated to Keyhole limpet hemocyanin (KLH), Asp Lys Ser Thr Val His Asp Gln Glu His Ile Met Glu His Leu Glu Cys KLH
(amino acid sequence 15-30 in SEQ ID No. 4)

His Lys Glu Glu Gly Ser Glu Gln Val Pro Pro Met Ser Glu Asp Glu Cys-KLH
(amino acid sequence 74-89 in SEQ ID No. 4)

KLH-Cys Asp Gly Tyr Ile Asp Tyr Ala Glu Phe Ala Lys Ser Leu Gln
(amino acid sequence 106-119 in SEQ ID No. 4)

and immunized rabbits as an immunogen to obtain serum after measuring levels of antibody to the protein. Anti-SDNSF polyclonal antibodies were purified using affinity column, in which each peptide fragment used as an immunogen was bound.

Example 8

Investigation of Secretory Pathway of SDNSF

Modified SDNSF proteins, which were tagged with inserted FLAG at N terminus (FLAG-SDNSF) or with FLAG-6His at C terminus (SDNSF-C'FLAG-6His) of rat SDNSF, were expressed in 293 T cells. The secretion of these tagged SDNSF proteins into culture supernatant was examined with Western blot analysis using both anti-SDNSF and anti-FLAG antibodies (FIG. 3).

Example 9

Localization of Rat SDNSF

Total RNA was extracted from adult rat brain, heart, lung, liver, spleen, kidney, testis, skeletal muscle and thymus with TRI$_{zol}$ reagent™ (purchased from Life Technologies, Inc), and poly(A)$^+$ RNA was purified with Oligotex-dT30<Super>™ (purchased from Roche).

Figure 4:
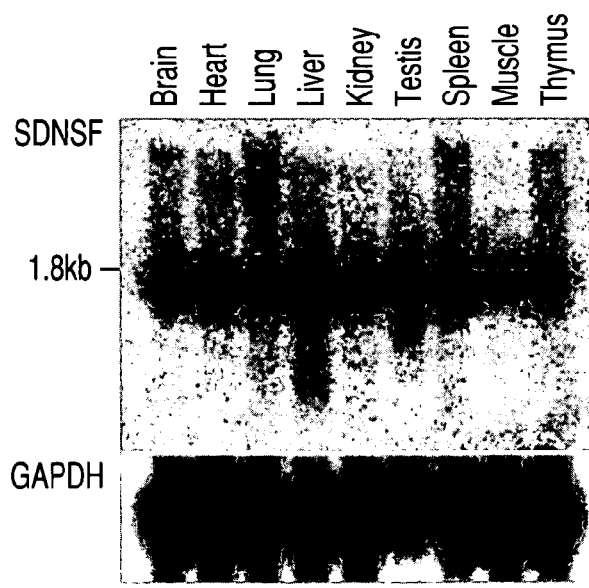
FIG. 4 is the result of blotting with the cDNA fragment $^{32}$P-labeled and purified by gel as a probe.

The poly(A)$^+$ RNA from various tissues were subjected to formaldehyde-gel electrophoresis and blotting according to the method of Sambrook et al. (Molecular Cloning (1989)). The detection using gel-purified and $^{32}$P-labelled cDNA fragment as a probe revealed that SDNSF were expressed in all tissues tested as shown in FIG. 4.

Figure 5:
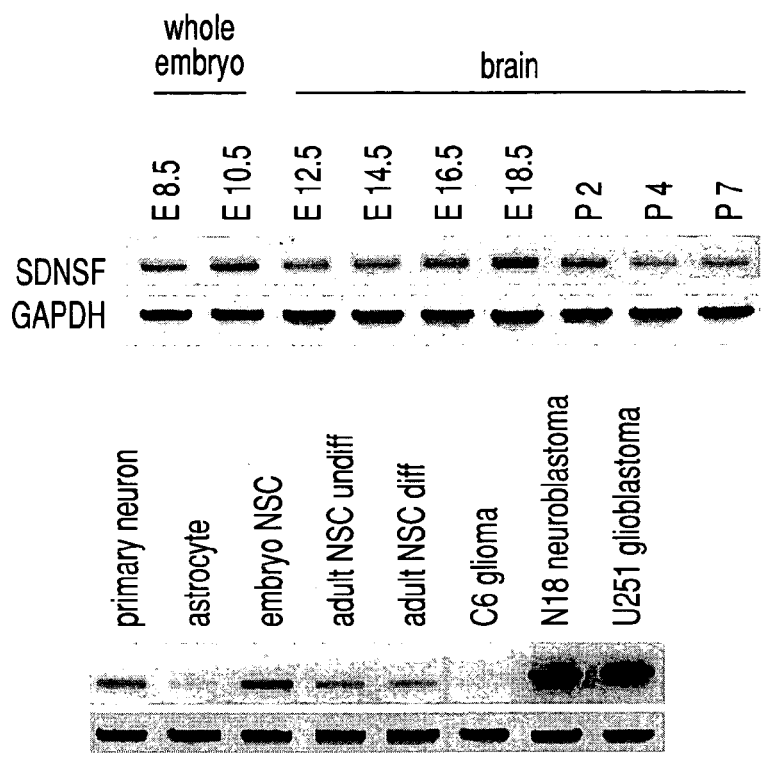
FIG. 5 shows the expression of SDNSF mRNA in primary neurons, astrocytes, neural stem cells (embryo NSCs, adult NSCs undifferentiated and adult NSCs differentiated), rat glioma C6, mouse neuroblast N18 and human glioblastoma UG251.
Figure 6:
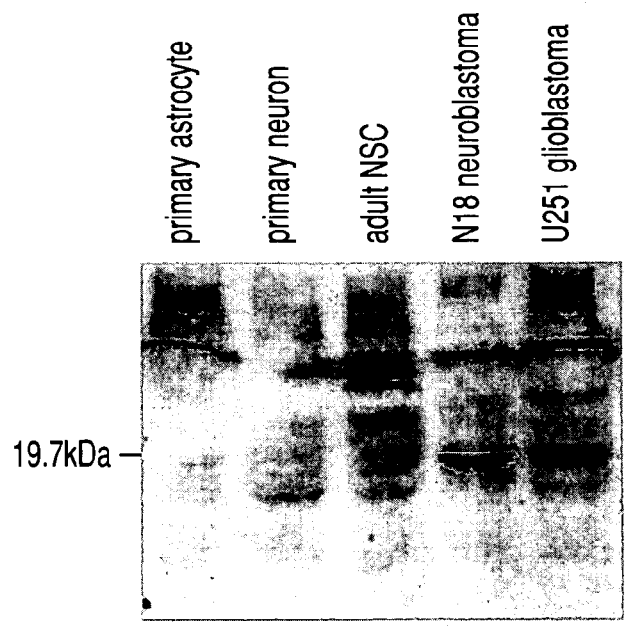
FIG. 6 shows the expression of SDNSF protein in primary astrocytes, primary neurons, adult NSCs, mouse neuroblast N18 and human glioblastoma UG251, FIG. 7 (A) (B) shows the effect of SDNSF addition on the survival of hippocampal neurons and neural stem cells.

Total RNA was extracted from rat whole embryo and embryonic brain, brain up to postnatal day 7, primary neurons and cell lines with TRI$_{zol}$ reagent™ (purchased from Life Technologies, Inc), and mRNA expression were examined by using RT-PCR. As shown in FIG. 5, the SDNSF transcript was expressed in cultured stem cells, primary neurons and neural stem cells. The SDNSF transcript was also expressed in human glioblastoma UG251 cells and mouse neuroblastoma N18 cells, but not in primary glia cells and rat glioma C6 cells. Furthermore, the expression of SDNSF protein was detected in human glioblastoma UG251 cells and mouse neuroblastoma N18 cells by Western blot analysis (FIG. 6).

Example 10

Viability Assays of SDNSF on Neurons and Stem Cells

Based on the localization of SDNSF, biological effects of SDNSF on neurons and stem cells were examined.

Figure 7A:
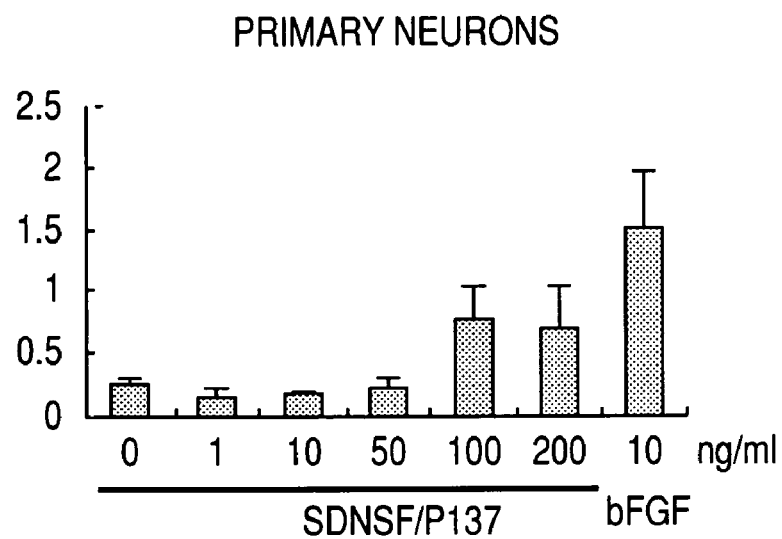
Figure 7B:
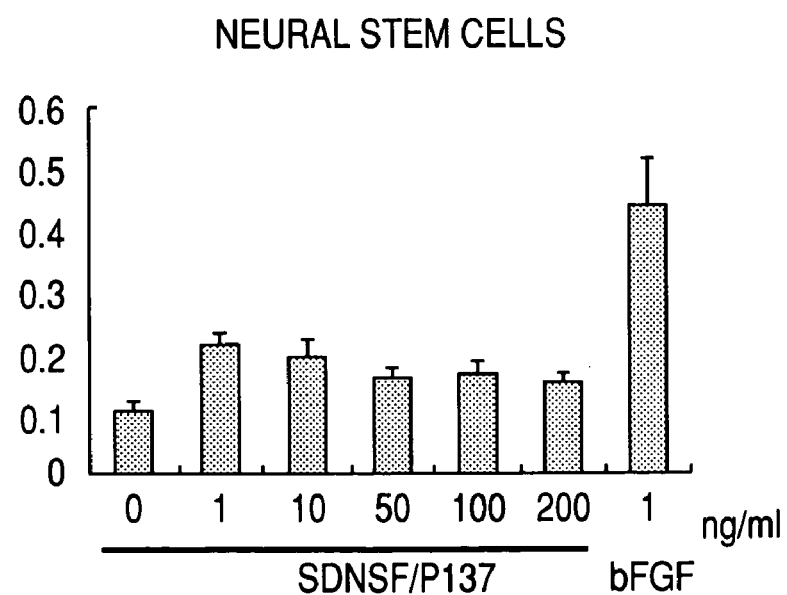
Figure 8:
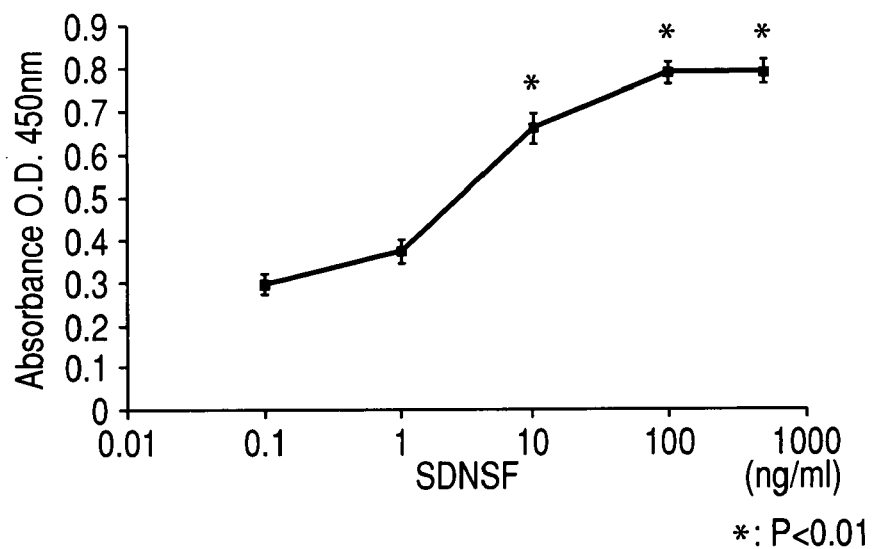
FIG. 8 shows that SDNSF improves hippocampal neurons viability in a dose dependent manner (Significant differences versus control are indicated by an asterisk (*) ($P<0.01$))
Figure 9:
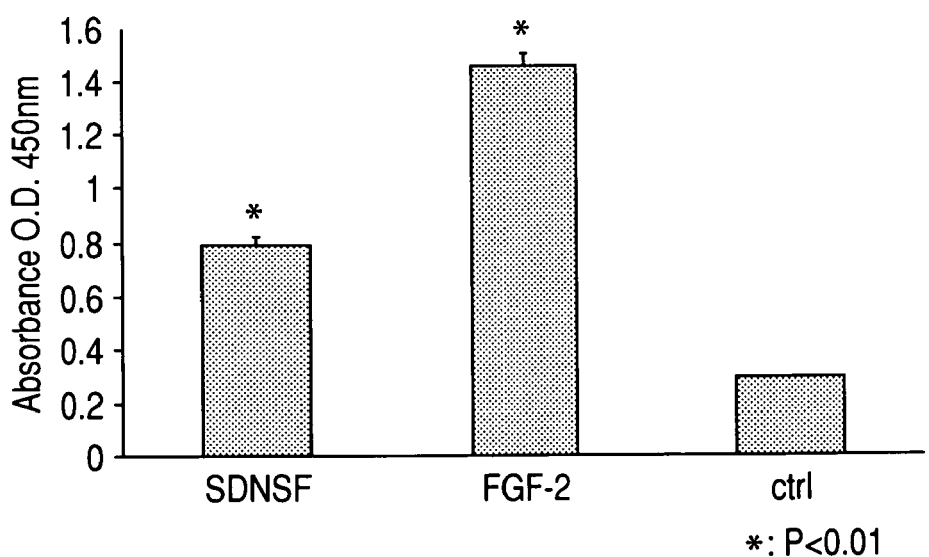
FIG. 9 shows the effect of SDNSF on the survival of neural stem cells cultured in the absence of FGF-2 (Significant differences versus control are indicated by an asterisk (*) ($P<0.01$))

Modified SDNSF protein (SDNSF-FLAG-6His), which was purified by using Ni-NTA method utilizing His structure in the molecule, was added to the cultures of rat primary hippocampal neurons and neural stem cells derived from rat hippocampus, and WST reduction assay was performed to measure the number of viable cell at day 4. As shown in FIG. 7, in primary neurons, SDNSF at the concentration of 100 ng/ml was effective on cell survival as compared with control group. In neural stem cells, it was shown that SDNSF tended to improve viable cell numbers as compared with control group. It was also shown that SDNSF improved the viability of neural stem cells derived from rat hippocampus in a dose-dependent manner when cells were cultured in FGF-2 (fibroblast growth factor-2) minus growth medium for 5 days (FIGS. 8 and 9).

Example 11

Figure 10:
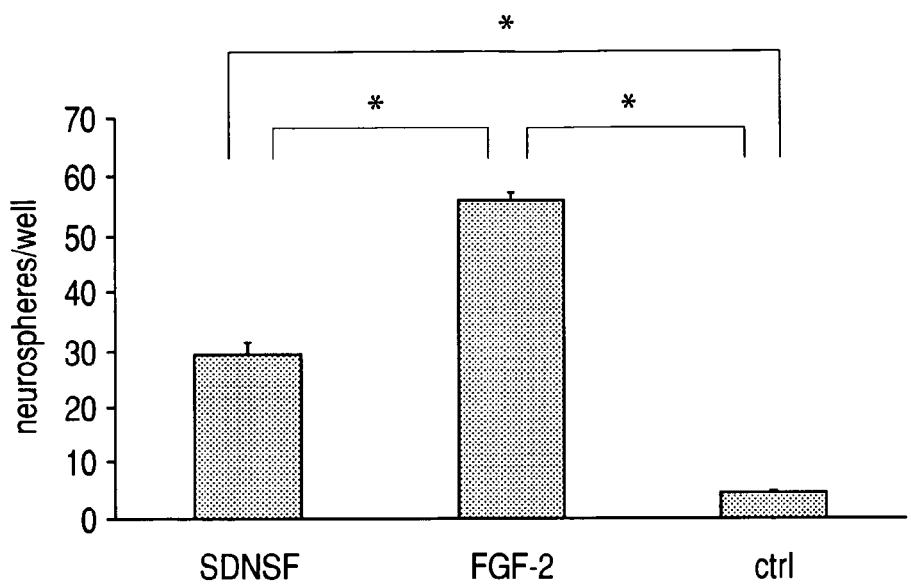
FIG. 10 shows the effect of SDNSF on self-renewal of neural stem cells by counting neurospheres formed in the absence of FGF-2 (Significant differences versus control are indicated by an asterisk (*) ($P<0.01$))
Figure 11:
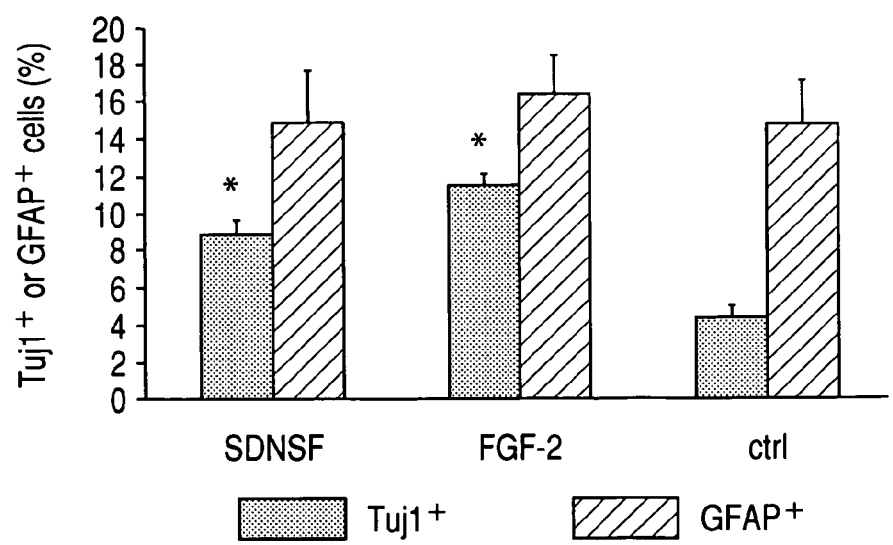
FIG. 11 shows the effect of SDNSF on the differentiation of neural stem cells into neurons in the neurospheres formed in the presence of SDNSF without FGF-2 (Significant differences between SDNSF-treated, FGF-2-treated and control groups are indicated by an asterisk (*) ($P<0.01$)).

Test for SDNSF's Effect on Self-Renewal and Differentiation of Neural Stem Cells After neural stem cells derived from rat hippocampus were cultured in the SDNSF$^+$/FGF-2$^-$ medium for 5 days, cells were replated on noncoated plates and grown for 6 days in growth medium containing FGF-2 (20 ng/ml), and the number of neurospheres were counted. A neuronal marker, Tuj-1-positive cells were also counted. AS shown in FIGS. 10 and 11, the number of neurospheres/well from SDNSF-treated group was significantly larger than that from the control group. Proportion of neurons in the neurospheres from SDNSF-treated group was significantly larger than that from the control group. These results indicated that SDNSF had activities for retaining self-renewal potentials of neural stem cells and for promoting the differentiation of neural stem cells into neuronal and glial phenotypes as well as FGF-2.

The invention claimed is:

1. A purified form of a polypeptide comprising the amino acid sequence shown in SEQ ID NO. 4 or 12.

2. The polypeptide according to claim 1 consisting of the amino acid sequence shown in SEQ ID NO: 4 or 12.

3. A process for producing a purified form of a polypeptide comprising the amino acid sequence shown in SEQ ID NO. 4 or 12, which comprises culturing a host cell transformed with a replication or expression vector comprising a cDNA encoding the polypeptide according to claim 1 under a condition effective to express the polypeptide.

* * * * *